US006682479B1

(12) United States Patent
Takahashi et al.

(10) Patent No.: US 6,682,479 B1
(45) Date of Patent: Jan. 27, 2004

(54) AIR FEEDING DEVICE FOR ENDOSCOPE

(75) Inventors: Noriaki Takahashi, Saitama-ken (JP); Satoshi Takami, Saitama-ken (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/494,470

(22) Filed: Jan. 31, 2000

(30) Foreign Application Priority Data

Feb. 2, 1999 (JP) .......................................... 11-024792

(51) Int. Cl.$^7$ ................................................ A61M 1/00
(52) U.S. Cl. ........................ 600/159; 600/158; 600/560; 604/26
(58) Field of Search ................................ 600/118, 158, 600/159, 560; 604/26; 417/94.2, 307, 12, 26

(56) References Cited

U.S. PATENT DOCUMENTS

| | | | |
|---|---|---|---|
| 4,201,517 A | * 5/1980 | Ferguson | ...................... 417/12 |
| 4,971,034 A | * 11/1990 | Doi et al. | .................... 600/158 |
| 5,006,109 A | * 4/1991 | Douglas et al. | ................ 604/26 |
| 5,360,396 A | * 11/1994 | Chan | ............................. 604/26 |
| 5,515,860 A | * 5/1996 | Aviv et al. | ................... 600/560 |
| 5,676,155 A | * 10/1997 | Novak et al. | ................ 600/560 |

FOREIGN PATENT DOCUMENTS

WO          94/23644          10/1994

* cited by examiner

*Primary Examiner*—John Mulcahy
(74) *Attorney, Agent, or Firm*—Greenblum & Bernstein, P.L.C.

(57) ABSTRACT

An air feeding device for an endoscope, is provided with a pressure control system that controls a pressure of air within a sealed space so as to fall within a predetermined set range. The air feeding device is further provided with an abnormal condition detecting system that detects an abnormal condition of at least one of the pressure within the sealed space and control of the pressure control system. Further, the air feeding device includes a resolving system that resolves the abnormal condition when the abnormal condition detecting system detects an abnormal condition.

15 Claims, 8 Drawing Sheets

FIG. 8A

==== ERROR ! ==== <001>
PRESSURE LIMIT OVER

FIG. 8B

==== ERROR ! ==== <002>
CONTROL TIME OVER

AIR FEEDING DEVICE FOR ENDOSCOPE

BACKGROUND OF THE INVENTION

The present invention relates to an air feeding device for an endoscope, and in particular, to a safeguard system of an air feeding device.

Conventionally, an air feeding device for an endoscope has been known. The air feeding device has an air compressor which compresses the air within a sealed space, and by opening/closing a valve connected to the sealed space, the air is fed to the human body cavity through a tube such as a forceps channel of an endoscope. In such an air feeding device, an operator sets a desired pressure of the air in advance, and the air compressor and the valve are controlled such that the actual discharge pressure meets the pressure set by the operator.

If the compressor, the valve, or an electric circuitry malfunctions during operation, the pressure of the sealed space may become extremely high. If the air leaks from the sealed space, the pressure within the sealed space remains low and may not reach the pressure enabling the desired discharge pressure.

If the abnormal conditions as above are not appropriately dealt with, the following problems would occur: if the pressure of the sealed space is extremely high, the sealed space may be deteriorated due to a high pressure, or the human cavity may be destroyed due to a high discharge pressure of the air; and if the air leaks from the sealed space, the air feeding device itself may be broken since the pressure within the sealed space remains low even if the compressor is driven for a long period.

SUMMARY OF THE INVENTION

It is therefore an object of the invention to provide an air feeding device for an endoscope, for preventing the abnormal condition of the air feeding device.

For the above object, according to the present invention, there is provided an air feeding device for an endoscope, which is provided with:

a pressure control system that controls a pressure of air within a sealed space so as to fall within a predetermined set range;

an abnormal condition detecting system that detects an abnormal condition of at least one of the pressure within the sealed space and control of the pressure control system;

a resolving system that resolves the abnormal condition when the abnormal condition detecting system detects an abnormal condition.

Since the resolving system immediately resolves the abnormal condition, a dangerous condition, e.g., a condition where a human cavity is exposed to a danger can be avoided.

In particular case, the abnormal condition detecting system may detect whether the pressure within the sealed space exceeds a predetermined upper limit.

It is preferable that, in the above case, the upper limit is a maximum pressure of a pressure range at which the air discharged from the endoscope would not hurt a human cavity.

Optionally or alternatively, the abnormal condition detecting system may detect whether the pressure control system controls the pressure within the sealed space to fall in the predetermined set range within a predetermined period of time.

When the abnormal condition is detected, the resolving system decreases the pressure within the sealed space. Since the pressure in the sealed space is decreased regardless of the type of the abnormal condition, a human cavity may not be exposed to danger.

Optionally, the resolving system terminates operation of the air feeding device. Therefore, the air feeding device may not be broken due to the abnormal condition.

Optionally, the air feeding device may be provided with a warning system that indicates occurrence of the abnormal condition.

The warning system indicates the occurrence of the abnormal condition by sound, by light and/or by displaying characters.

When the abnormal condition is indicated by displaying the characters, a type of the occurred abnormal condition may be indicated.

According to another aspect of the invention, there is provided an air feeding device for an endoscope, which is provided with:

a compressing system that compresses air within a sealed space;

a pressure measuring device that measures a current pressure of the sealed space;

a pressure control valve provided between the sealed space and outside, a pressure within the sealed space being decreased by opening the pressure control valve;

a pressure control system that controls the compressing system and the pressure control valve so that the pressure within the sealed space falls within a predetermined set range;

an abnormal condition detecting system that detects an abnormal condition of at least one of the pressure within the sealed space and control of the pressure control system; and a resolving system that resolves the abnormal condition when the abnormal condition detecting system detects an abnormal condition.

Optionally, the pressure control system controls the pressure control valve to open when the pressure within the sealed space is greater than an upper limit of the predetermined set range, and wherein the pressure control system controls the compressing system to compress the air within the sealed space if the pressure within the sealed space is less than a lower limit of the predetermined set range.

Further, the resolving system controls the pressure control valve to open when the abnormal condition detection system detects the abnormal condition.

Furthermore, the resolving system controls the compressing system to stop compressing the air within the sealed space.

DESCRIPTION OF THE ACCOMPANYING DRAWINGS

FIG. 1 schematically shows an air feeding system employing a safeguard system according to an embodiment of the invention;

FIG. 2 is a rear view of the air feeding device shown in FIG. 1;

FIG. 3 schematically shows an arrangement of main elements inside the air feeding device shown in FIG. 1 when viewed from the top;

FIGS. 8A and 8B show examples of indications of the abnormal conditions.

DESCRIPTION OF THE EMBODIMENTS

Hereinafter, the invention will be described with reference to the accompanying drawings.

Figure 1:
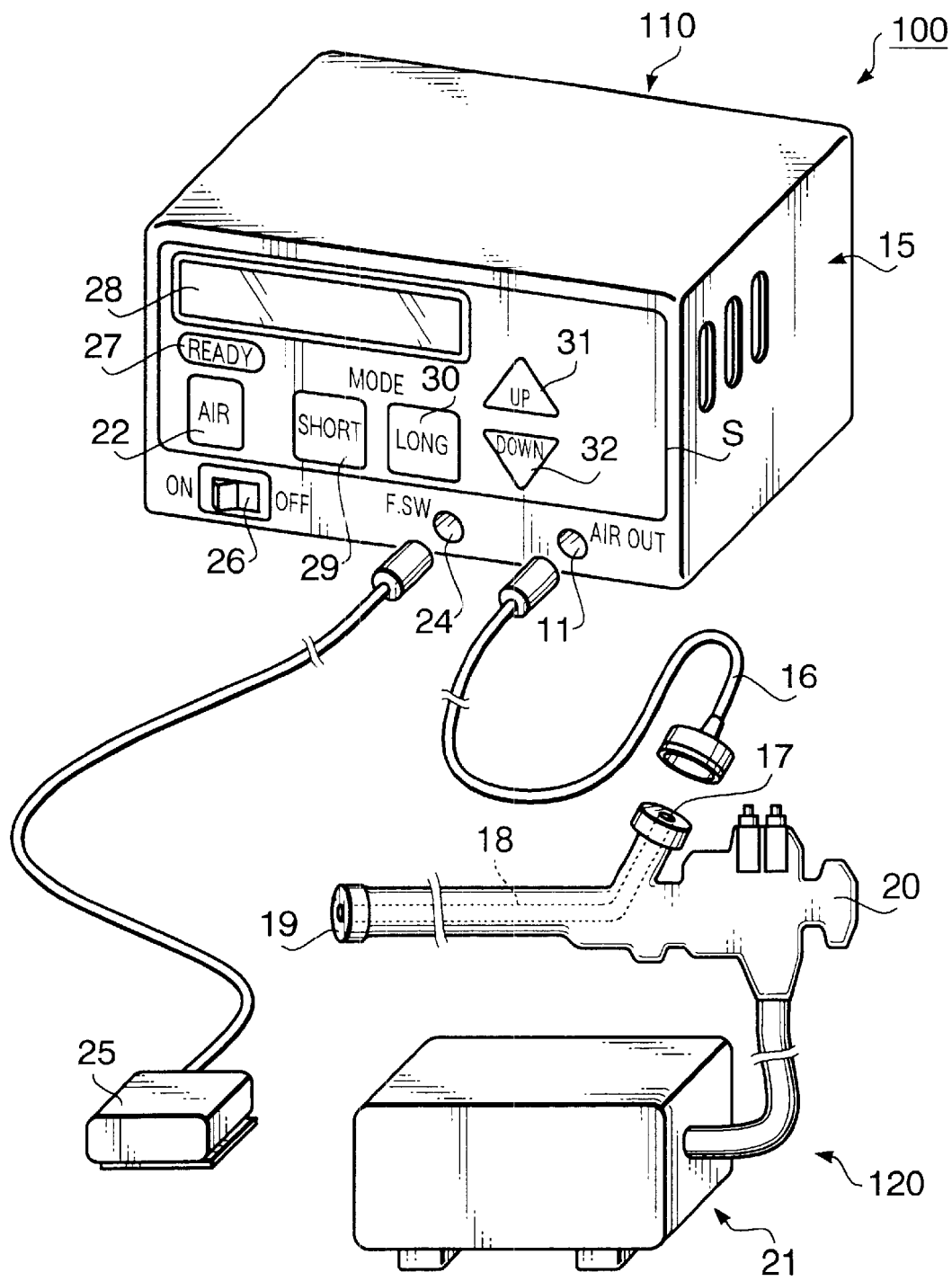

FIG. 1 schematically shows an entire air feeding system 100 according to an embodiment of the present invention.

The air feeding system 100 is provided with an air feeding device 110, and an endoscope system 120. The air is fed by the air feeding system 100 onto the wall of the body cavity for diagnosing thereof.

The air feeding device 110 has a casing 15, on which an operation panel S, a main switch 26, connection ports 11 and 24 are provided.

The main switch 26 is a switch for powering ON/OFF the electrical circuits of the air feeding system 110.

On the operation panel S, an air feeding switch 22 is provided. The air feeding switch 22 is for discharging the air enclosed in a sealed space, which is formed inside the air feeding device 110, to outside thereof. That is, when the air feeding switch 22 is operated, the air is discharged from the connection port 11.

Further, on the operation panel S, a stand-by lamp 27, and a display 28 are provided. The stand-by lamp 27 is lit, when the pressure in the sealed space has reached a pressure at which the air is discharged at a desired pressure, to indicate discharging of the air is ready. The display 28 displays, by alphanumerical characters, information such as the set pressure (a target discharge pressure) of the air. Furthermore, on the operation panel S, a short pulse switch 29, a long pulse switch 30, an UP switch 31 and a DOWN switch 32 are provided.

The short pulse switch 29 is used when the air is to be discharged for a relatively shorter period of time. The long pulse switch 31 is a switch for discharging the air for a relatively longer period of time. In this embodiment, when the short pulse switch 29 is depressed, the air is discharged for 60 msec. (milliseconds), while when the long pulse switch 30 is depressed, the air is discharged for one second. The UP and DOWN switches 31 and 32 are used for setting the pressure of the discharged air.

The endoscope system 120 includes an endoscope 20 and an image processor 21. The endoscope 20 is formed with a forceps channel 18. In this system, the air discharged from the air feeding device 110 is introduced in and flows through the forceps channel 18. In order to introduce the air from the air feeding device 110 to the forceps channel 18, a connection tube 16 is used. An end of the connection tube 16 is connected to the connection port 11 of the air feeding device 110, and the other end of the connection tube 16 is connected to the inlet 17 of the forceps channel 18. Thus, the air discharged from the air feeding device 110 flows in the connection tube 16 and the forceps channel 18, and is discharged out of an outlet 19 of the forceps channel 18.

The image processor 21 includes an imaging device (not shown) for capturing an optical image formed by the endoscope 20 and output an image signal, an signal processing device (not shown) for processing the image signal, and a display device (not shown) for displaying an image in accordance with the image signal output from the image processing device.

To the connection port 24, a cable of a foot switch 25 for controlling discharge of the air by foot is connected.

Figure 2:
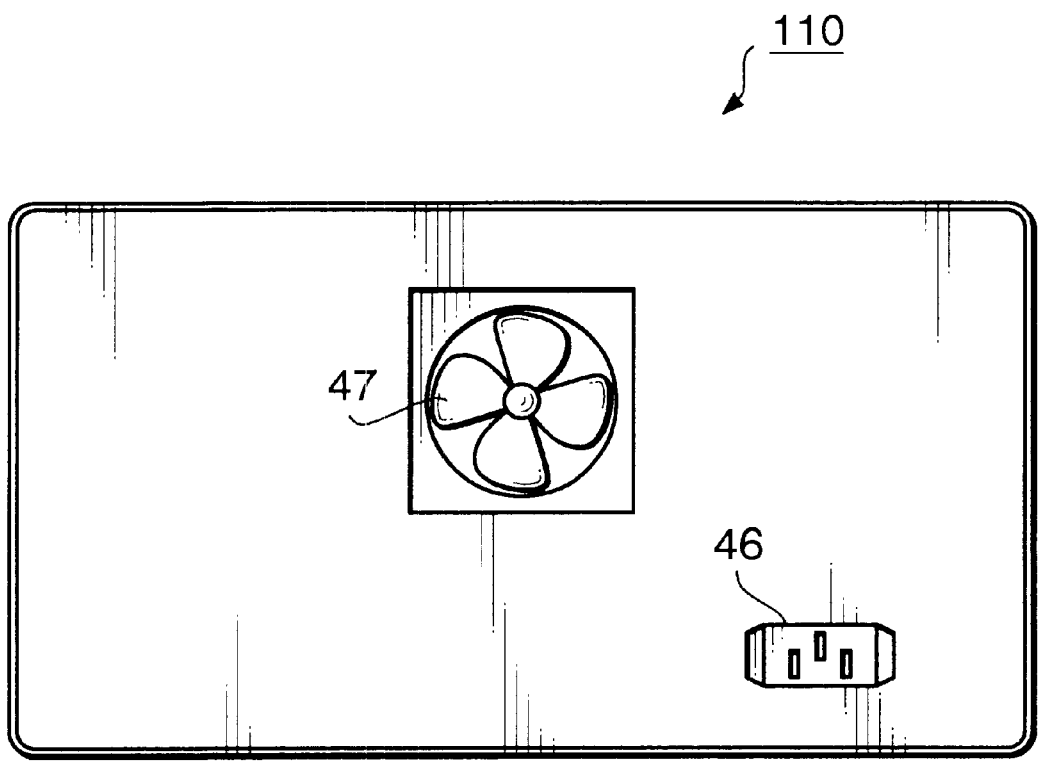

FIG. 2 is a rear view of the air feeding device 110. As shown in FIG. 2, a DC fan 47 for cooling the device 110, and an AC inlet 46 to be connected to a commercial electric power source are provided.

Figure 3:
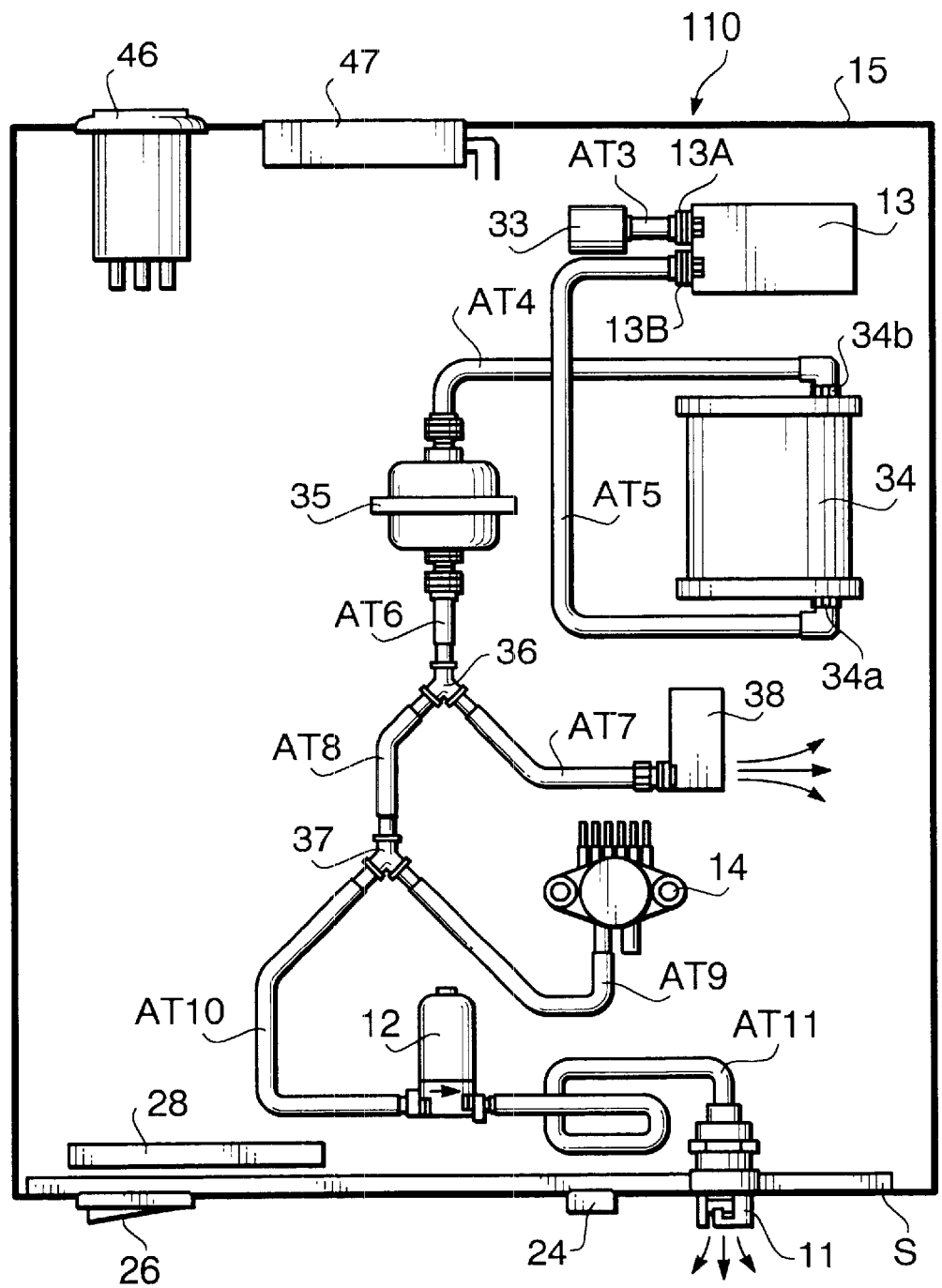

FIG. 3 schematically shows an arrangement of main elements inside the air feeding device 110, when an upper panel thereof is removed and viewed from the top. For the sake of simplicity, electrical circuits and wires are omitted in FIG. 3. As described above, on a wall of the casing 15, the AC inlet 46, the DC fan 47, the main switch 26, the operation panel S provided with the display 28, the connection port 11, and the connector 24 are provided.

Inside the casing 15, a sealed space for feeding the air is formed. Specifically, the sealed space is formed by: a compressor 13, an air tube AT5, an air tank 34, an air tube AT4, an air filter 35, an air tube AT6, a Y-joint 36, an air tube AT7, a pressure control valve 38, an air tube AT8, a Y-joint 37, an air tube AT9, a pressure sensor 14, an air tube AT10, and a discharging valve 12. The air enclosed in the sealed space is discharged from the connection port 11 via the air tube AT11.

At a portion between the air filter 35 and the discharging valve 12, the sealed space is branched towards the pressure control valve 38 by the joint 36 and the air tube AT7, and by the joint 37 and the air tube AT9, the sealed space is branched towards the pressure sensor 14. It should be noted that the air tubes AT6, AT7 and AT8 communicate with each other through the joint 36. Further, the air tubes AT8, AT9 and AT10 communicate with each other through the joint 37.

The air enclosed in the sealed space is discharged when the pressure is adjusted, and the air is fed to the body cavity. The pressure control valve 38 is used for the former purpose, i.e., the pressure control valve 38 only opens when the pressure of the air in the sealed space is reduced. The discharging valve 12 is usually closed, and is opened only when the air feeding switch 22 or the foot switch 25 is operated.

In the embodiment, a silencer 33 is provided for reducing noise when the compressor 13 operates. Specifically, the silencer 33 is coupled to the air intake 13A of the compressor 13 via the air tube AT3. When the compressor 13 starts operating, the air is introduced, via the silencer 33 and the air tube AT3, from the intake 13A of the compressor 13, and fed into the sealed space through an outlet 13B of the compressor 13, thereby the pressure in the sealed space is increased.

The air tank 34 is provided for enlarging the volume of the sealed space. The volume of the air tank 34 is much larger than the sum of the volumes of the air tubes AT4 through AT10. The airtank 34 is provided with connectors 34a and 34b on opposite surfaces, respectively, and the air tube AT5, which connects the outlet 13B of the compressor 13, is connected to the connector 34a which is located farther from the compressor 13 than the connector 34b is.

The air filter 35 removes the dust existing in the sealed space.

The pressure inside the sealed space is measured by the pressure sensor 14.

When the main switch 24 is turned ON, the compressor 13 and the pressure control valve 38 are driven to adjust the pressure in the sealed space in accordance with a set pressure. Specifically, if the pressure inside the sealed space (which will be referred to as an actual sealed space pressure Ps), which is detected by the pressure sensor 14, is lower than a pressure (which will be referred to as an objective pressure Po) for obtaining the set discharge pressure (which will also be referred to as the target discharge pressure Pt), the compressor 13 is driven and the pressure control valve 38 is closed. If the pressure inside the sealed space is higher than the objective pressure Po, the compressor 13 stops operating, and the pressure control valve 38 is opened. If the pressure Ps inside the sealed space coincides with the objective pressure Po, the compressor 13 does not operate, and the pressure control valve 38 is closed.

The discharging valve 12 operates in response to operation of the air feeding switch 22 or the foot switch 25. When the discharging valve 12 opens, the air is discharged from the connection port 11 via the air tube AT11.

Figure 4:
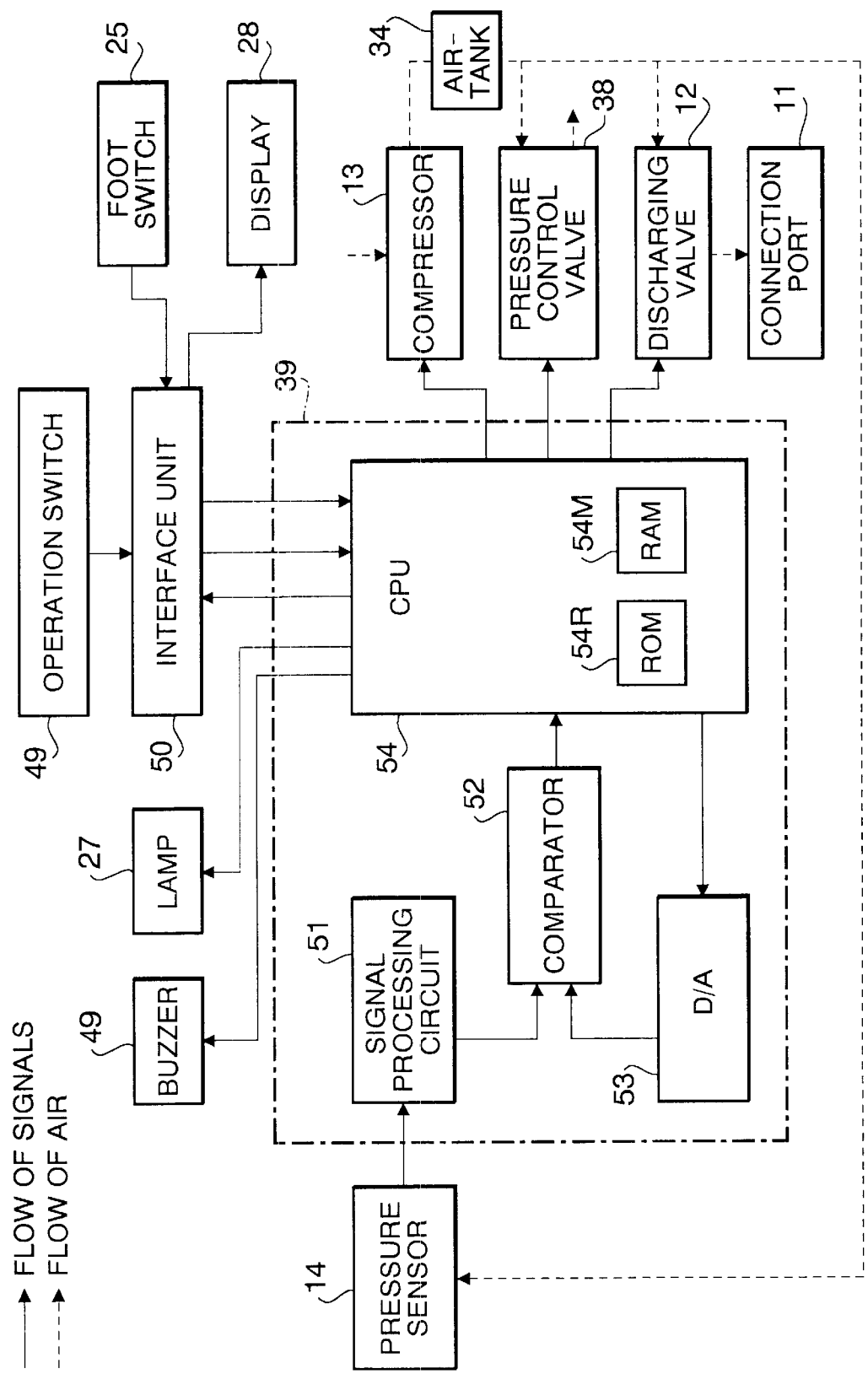
FIG. 4 is a block diagram illustrating a control system of the air feeding device as well as a flow of the air therein according to the embodiment.

FIG. 4 is a block diagram illustrating a control system of the air feeding device 110 according to the embodiment. A flow of the air is also indicated in FIG. 4. The control system is provided with a controller 39, which includes a signal processing circuit 51, a voltage comparator 52, a D/A converter 53, and a CPU (Central Processing Unit) 54. The controller 39 controls the operation of the entire system of the air feeding device 110. The CPU 54 outputs driving signals to the piezo-electric buzzer 49, a lamp 27, the compressor 13, the pressure control valve 38, and the discharging valve 12.

An operation switch 49 outputs predetermined signals in response to the operation of the air feeding switch 22, the short pulse switch 29, the long pulse switch 30, the UP switch 31 or the DOWN switch 32 (see FIG. 1). The signals generated by the operation switch 49 and the foot switch 25 are transmitted to the CPU 54 via an interface unit 50. The interface unit 50 applies predetermined signal processing/converting operations and outputs signals suitable to be processed by the CPU 54. The interface unit 50 determines the currently set discharge pressure in accordance with the signals generated in response to the operation of the UP and DOWN switches 31 and 32, and controls the display 28 to display the alphanumerical characters indicating the same.

The signal output by the pressure sensor 14 is input into the signal processing circuit 51, and a predetermined signal processing operation (e.g., noise reduction) is applied. Then, the processed signal is input into one port of the voltage comparator 52. The signal representing the target discharge pressure Pt set by the UP and DOWN switches 31 and 32 is converted into a signal representing the objective pressure Po in the sealed space, and is transmitted from the CPU 54 to the D/A converter 53 which outputs an analog voltage value. The analog voltage value output by the D/A converter 53 is input to the other input port of the voltage comparator 52.

The voltage comparator 52 compares the voltage output by the signal processing circuit 51 and the voltage output by the D/A converter 53. The voltage comparator 52 outputs a difference between the voltage values. The voltage difference is converted into a signal having a value which can be processed by the CPU 54, then the converted signal representing the voltage difference is transmitted to the CPU 54. The CPU 54 temporarily stores the transmitted signal in a RAM 54M as comparison data.

When a trigger signal is input in response to operation of the UP switch 31 or DOWN switch 32, the CPU 54 determines whether the pressure Ps in the sealed space is equal to the objective pressure Po in accordance with the comparison result stored in the RAM 54M. If the pressure Ps in the sealed space is different from the objective pressure Po, the CPU 54 drives the compressor 13 and/or the pressure control valve 38 to adjust the pressure Ps in the sealed space so as to coincide with the objective pressure Po.

It should be noted that, if the voltages compared by the comparator 52 are different but substantially equal, the operation of the compressor 13, and opening/closing of the pressure control valve 38 may repeats within a relatively short period of time (i.e., a so-called hunting phenomenon). In order to avoid such a situation, the comparator 52 is constituted to have a predetermined dead band.

Further, if the pressure within the sealed space is too high, the discharged air may hurt the human cavity. In the embodiment, an upper limit PL of a predetermined allowable pressure range at which the discharged air does not hurt the human cavity is stored in a ROM 54R of the CPU 54. In the embodiment, the pressure within the sealed space is periodically monitored to avoid an abnormal condition where the pressure is extremely high (i.e., the pressure is greater than the upper limit of the allowable range). The upper limit PL is, for example, 1.0 (kgf/m$^2$). It should be noted that the value is only an example, and it should be determined for individual systems. Control when the abnormal condition occurs will be described in detail later.

The lamp 27 is lit when the air feeding device 110 is in the stand-by condition.

According to the embodiment, if the pressure within the sealed space becomes extremely high and/or the pressure within the sealed space does not reach the target pressure Pt within a predetermined period of time, the CPU 54 judges that an abnormal condition has occurred. In such a case, the piezo-electric buzzer 49 is driven and/or the lamp 27 blinks and/or a warding message is displayed in the display 28.

Figure 5:
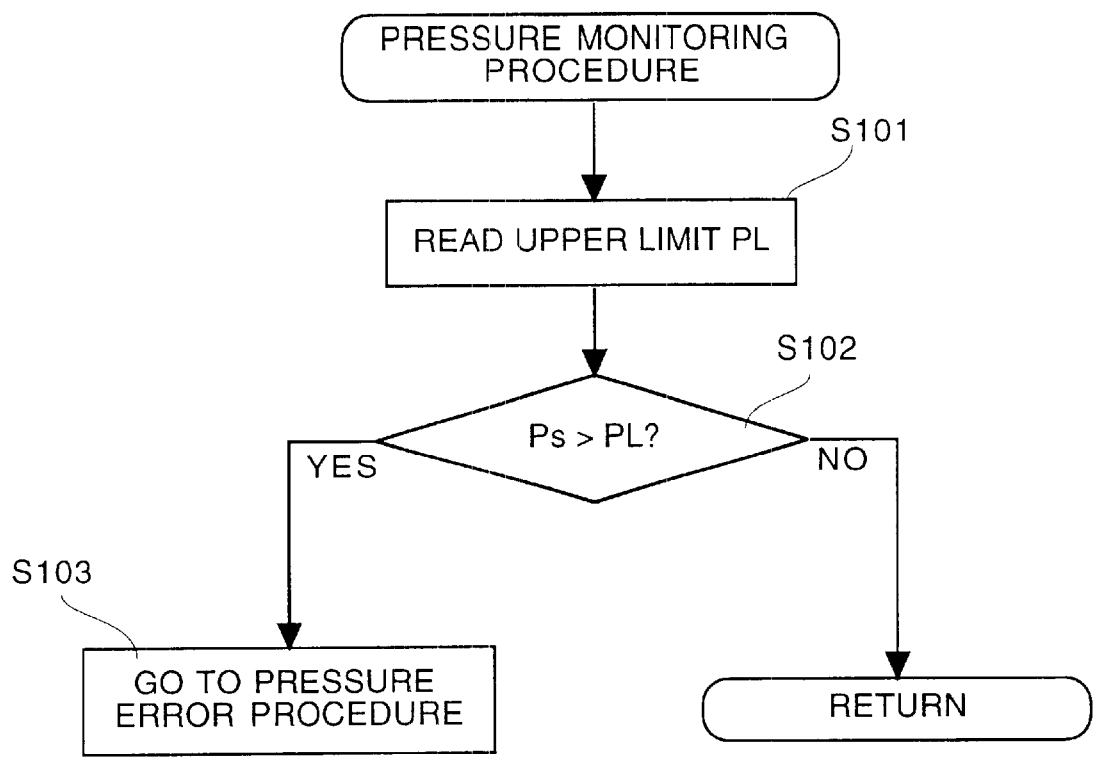
FIGS. 5 is a flowchart illustrating a pressure monitoring procedure for monitoring whether a pressure within the sealed space is less than an upper limit.

FIG. 5 is a flowchart illustrating a pressure monitoring procedure for monitoring whether the pressure within the sealed space exceeds the predetermined upper limit. The pressure monitoring procedure is an interruption procedure that is executed, independently of other procedures for operation, at every predetermined interval.

In S101, the CPU 54 reads out the upper limit PL of the pressure within the sealed space from the ROM 54R. Then, in S102, it is judged whether the current pressure output from the signal processing circuit 51 exceeds the upper limit PL. If the current pressure is greater (S102: YES), then control proceeds to S103 where control proceeds to a pressure error procedure shown in FIG. 7. If the current pressure is not greater than the upper limit PL (S102: NO), the interruption shown in FIG. 5 is terminated.

Figure 6:
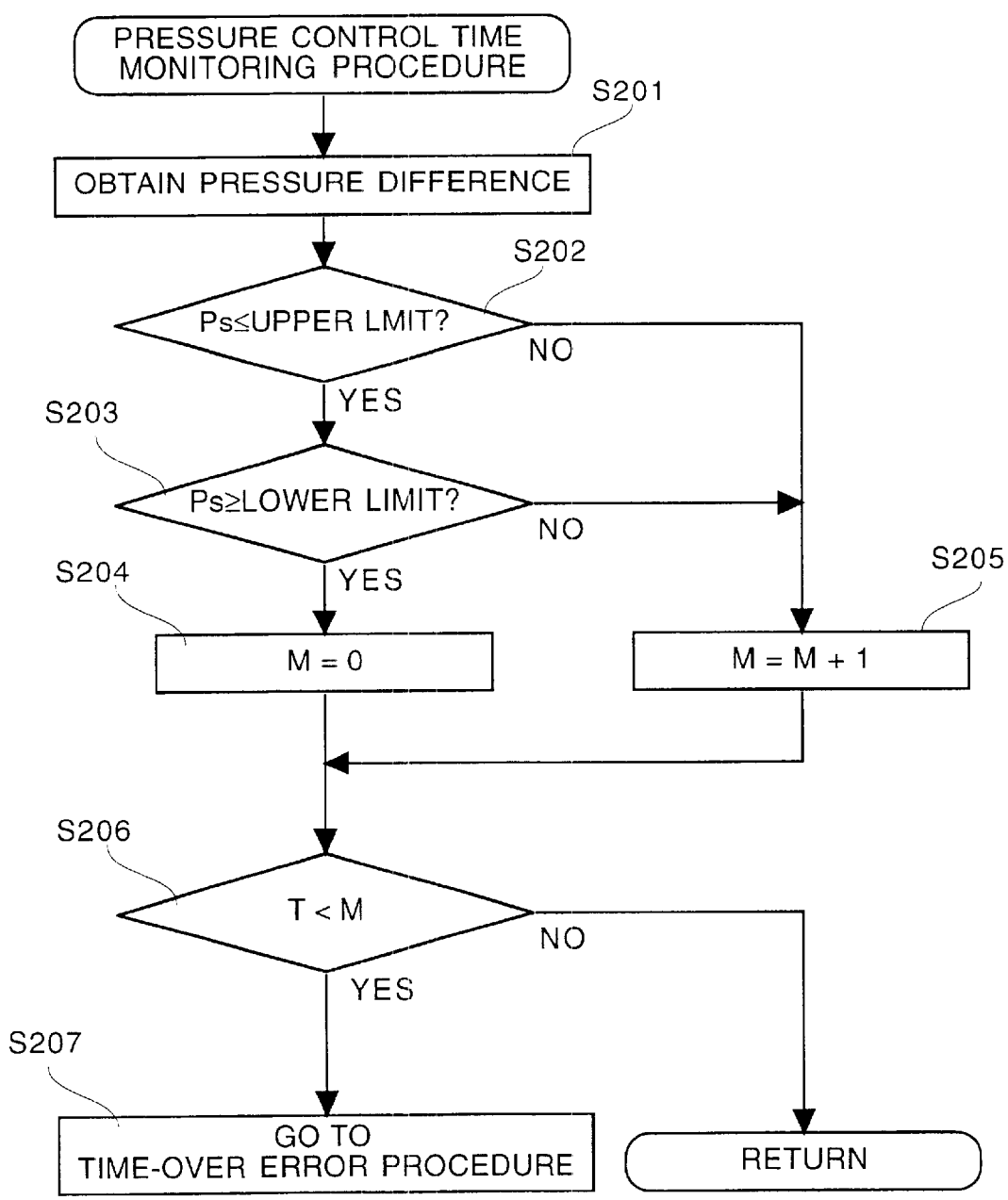
FIGS. 6 is a flowchart illustrating a pressure control period monitoring procedure for monitoring whether the pressure adjustment is performed within an allowable period.

FIG. 6 shows a flowchart illustrating a pressure control time monitoring procedure for monitoring whether the pressure within the sealed space is adjusted within a predetermined period of time. The pressure control time monitoring procedure is also an interruption which is executed independently of the other procedures. The procedure is executed, for example, at every ¹⁄₁₀₀ seconds.

In S201, a pressure difference of the current pressure Ps within the sealed space and the target pressure Pt is obtained.

In S202 and S203, it is judged whether the pressure difference is within a predetermined range that is defined for avoiding the hunting phenomenon.

If the pressure difference is within the predetermined range (S202: YES; and S203: YES), then a counter M is set to zero (0) in S204. If the pressure difference is out of the predetermined range (S202: NO; or S203: NO), the counter M is incremented by one (1) in S205.

In this embodiment, it is assumed that the pressure within the sealed space should reach within ten seconds. If the pressure PS within the sealed space does not reach the target pressure Pt within ten seconds, the CPU 54 judges that an abnormal condition has occurred.

As described above, the pressure control time monitoring procedure is executed at every $1/100$ seconds. Therefore, if the pressure difference does not fall within the predetermined range (i.e., S202: NO; and S203: NO), and the procedure is executed more than 1000 times, the CPU 54 judges that the abnormal condition has occurred. Thus, in S206 it is judged whether the counter M is greater than a threshold value T (i.e., 1000). If the counter M is greater than the threshold value T, control proceeds to a time-over error procedure shown in FIG. 7. If the counter M is not greater than the threshold value T (S206: NO), the pressure control time monitoring procedure is terminated.

It should be noted that the threshold value T should not be limited to 1000. The value T should be determined depending on individual systems employing the present invention.

Figure 7:
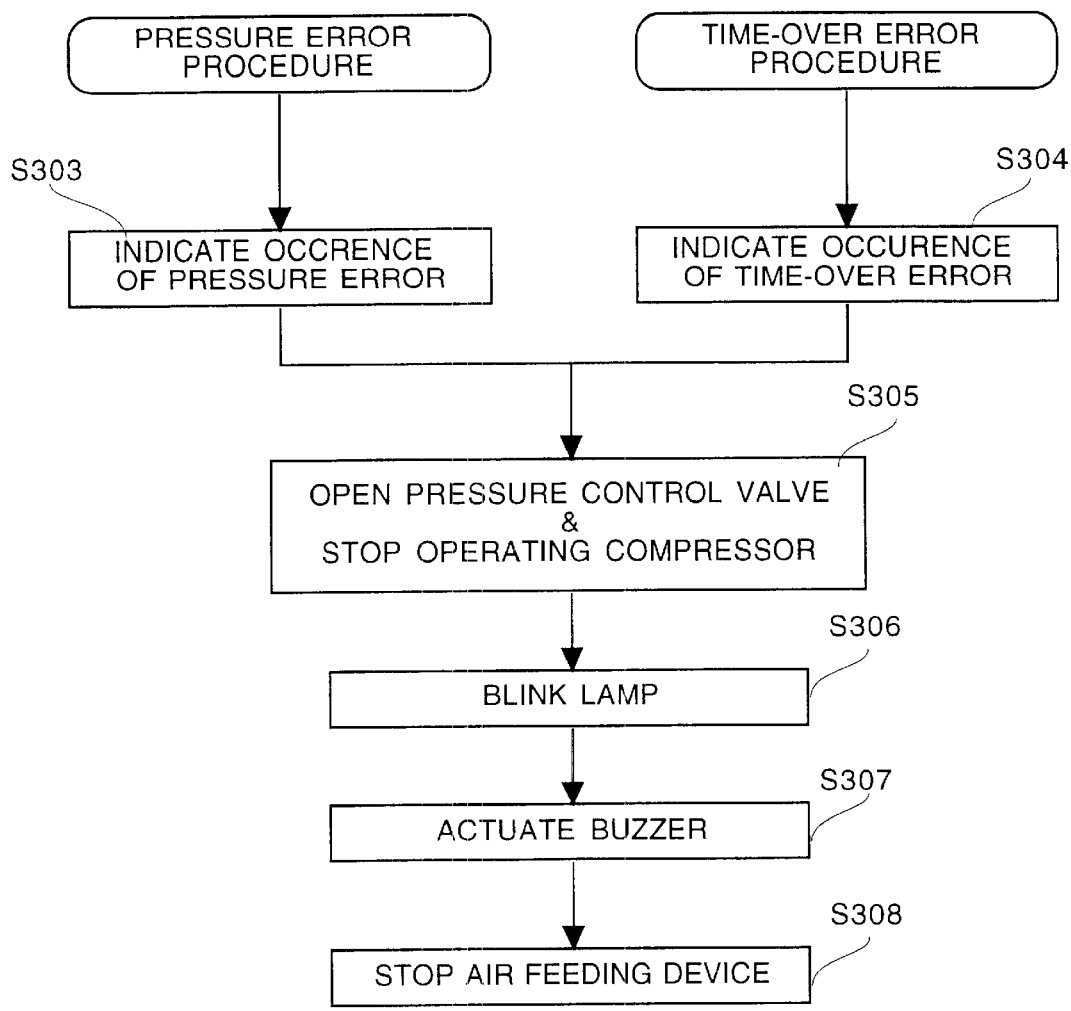
FIGS. 7 is a flowchart illustrating an abnormal condition resolving procedure for dealing with abnormal conditions of the air feeding device.

FIG. 7 is a flowchart illustrating the time-over error and the pressure error procedures.

In the embodiment, the time-over error procedure and the pressure error procedure are the same procedure except that different warning messages are displayed on the display 28.

When the pressure error procedure is executed, in S303, a message indicating that the pressure Ps within the sealed space exceeds the predetermined upper limit is displayed on the display 28. An example of such a message is shown in FIG. 8A. Then, control proceeds to S305.

When the time-over error procedure is executed, in S304, a message indicating that the pressure Ps within the sealed space has not been adjusted within a predetermined period (e.g., 10 seconds) is displayed on the display 28. An example of such a message is shown in FIG. 8B. Then, control proceeds to S305.

In S305, the pressure control valve 38 is opened, and the compressor 13 is stopped, thereby the pressure Ps within the sealed space decreases.

In S306, the lamp 27 is driven to blink to indicate that an abnormal condition has occurred. Alternatively, the lamp 27 may be continuously lit.

In S307, the piezo-electric buzzer 49 is actuated to indicate the occurrence of the abnormal condition by sound. The buzzer 49 may be actuated intermittently or continuously.

Further, in S308, the operation of the air feeding device 110 is terminated. That is, when an abnormal condition has occurred, the operation is terminated even though the main switch 26 is operated to power ON.

As described above, when the abnormal condition occurs, at least the pressure within the sealed space is decreased, and the operation of the air feeding device is automatically terminated, a dangerous condition can be avoided.

The present disclosure relates to the subject matter contained in Japanese Patent Application No. HEI 11-024792, filed on Feb. 2, 1999, which is expressly incorporated herein by reference in its entirety.

What is claimed is:

1. An air feeding device for an endoscope, comprising:

a pressure control system that controls a pressure of air within a sealed space defined within said air feeding device so as to fall within a predetermined set range;

an abnormal condition detecting system that detects an abnormal condition of at least one of the pressure within the sealed space and control of said pressure control system;

a resolving system that resolves the abnormal condition when the abnormal condition detecting system detects an abnormal condition; and a discharge valve configured to discharge an air pulse of a predetermined duration from said sealed space to said endoscope.

2. The air feeding device according to claim 1, wherein said abnormal condition detecting system detects whether the pressure within said sealed space exceeds a predetermined upper limit.

3. The air feeding device according to claim 2, wherein said upper limit is a maximum pressure of a pressure range at which the air discharged from the endoscope would not hurt a human cavity.

4. The air feeding device according to claim 1, wherein said abnormal condition detecting system detects whether said pressure control system controls the pressure within the sealed space to fall in the predetermined set range within a predetermined period of time.

5. The air feeding device according to claim 1, wherein said resolving system decreases the pressure within the sealed space.

6. The air feeding device according to claim 5, wherein said resolving system terminates operation of the air feeding device.

7. The air feeding device according to claim 1, further comprising a warning system that indicates occurrence of the abnormal condition.

8. The air feeding device according to claim 7, wherein said warning system indicates the occurrence of the abnormal condition by sound.

9. The air feeding device according to claim 7, wherein said warning system indicates the occurrence of the abnormal condition by light.

10. The air feeding device according to claim 7, wherein said warning system comprises a display device that displays the occurrence of the abnormal condition by characters.

11. The air feeding device according to claim 10, wherein said warning system indicates a type of the occurred abnormal condition by alphanumerical characters.

12. An air feeding device for an endoscope, comprising:

a compressing system that compresses air within a sealed space defined within said air feeding device;

a pressure measuring device that measures a current pressure of the sealed space;

a pressure control valve provided between the sealed space and outside, a pressure within said sealed space being decreased by opening said pressure control valve;

a pressure control system that controls said compressing system and said pressure control valve so that the pressure within the sealed space falls within a predetermined set range;

an abnormal condition detecting system that detects an abnormal condition of at least one of the pressure within the sealed space and control of said pressure control system;

a resolving system that resolves the abnormal condition when the abnormal condition detecting system detects an abnormal condition; and a discharge valve configured to discharge an air pulse of a predetermined duration from said sealed space to said endoscope.

13. The air feeding device according to claim 12, wherein said pressure control system controls said pressure control valve to open when the pressure within the sealed space is greater than an upper limit of the predetermined set range, and wherein said pressure control system controls said compressing system to compress the air within said sealed space if the pressure within the sealed space is less than a lower limit of the predetermined set range.

14. The air feeding device according to claim 13, wherein said resolving system controls said pressure control valve to open when said abnormal condition detection system detects the abnormal condition.

15. The air feeding device according to claim 14, wherein said resolving system controls said compressing system to stop compressing the air within said sealed space.

* * * * *